United States Patent [19]

Niego et al.

[11] Patent Number: 4,822,949

[45] Date of Patent: Apr. 18, 1989

[54] PRODUCTION OF HYBRID CUCUMBER SEEDS

[75] Inventors: Shlomo Niego, Maskeret Batia; Esra Galun; Margalith Levy, both of Rehovot, all of Israel

[73] Assignee: Yeda Research Development Company Limited, Rehovot, Israel

[21] Appl. No.: 39,896

[22] Filed: Apr. 20, 1987

[30] Foreign Application Priority Data

Apr. 20, 1986 [IL] Israel ........................................ 78745

[51] Int. Cl.$^4$ ............................................... A01H 1/02
[52] U.S. Cl. ........................................... 800/1; 47/58; 47/DIG. 1
[58] Field of Search ................... 800/1; 47/58, DIG. 1

[56] References Cited

U.S. PATENT DOCUMENTS 4,686,319  8/1987  Shifriss ..................................... 800/1

Primary Examiner—Robert E. Bagwill
Attorney, Agent, or Firm—Saidman, Sterne, Kessler & Goldstein

[57] ABSTRACT

The invention relates to the production of $F_1$ hybrid seeds in cucumber (*Cucumis sativus*). The present invention relates to a method wherein the pollen-parent bears only male flowers and thus lacks the capability to bear fruits. The method comprises planting the hybrid seed production field with a mixture of seed-parent and pollen-parent seeds and harvesting the desired $F_1$ hybrid cucumber seeds from the thus produced fruit on the seed parent.

This invention also relates to hybrid seed produced by the methods of this invention, the hybrid cucumber plant produced from the hybrid cucumber seed, and variants, modifications, and mutants thereof.

6 Claims, No Drawings

PRODUCTION OF HYBRID CUCUMBER SEEDS

FIELD OF THE INVENTION

This invention is in the field of plant breeding, specifically hybrid cucumber breeding.

BACKGROUND OF THE INVENTION

Field crops are bred through techniques that take advantage of the plant's method of pollination. A plant is self-pollinating if pollen from one flower is transferred to the same or another flower of the same plant. A plant is cross-pollinated if the pollen comes from a flower on a different plant. A plant is sib-pollinated if pollen from one flower is transferred to another flower of a related plant.

The $F_1$ hybrid seed of cucumber plants (*Cucumis sativus*) are produced through a seed parent and a pollen parent. In current cucumber breeding techniques, the seed parent is a gyneocious line, i.e., having only female flowers. The pollen parent is a monoecious line, i.e., having both male and female flowers. For some cucumber hybrids, the pollen plant may be andromonoecious, i.e., having both male and bisexual flowers, or hermaphroditic, i.e., having bisexual flowers.

The female seed parent must be cross-pollinated in order to produce fruits and the $F_1$ hybrid seeds. However, the pollen parent is capable of self- and sib-pollination, resulting in commercially useless fruits and seeds.

In order to isolate the $F_1$ hybrid of the female seed parent from the pollen parent fruit, the $F_1$ hybrid production fields are planted in separate rows: several seed-parent rows alternate with one or two pollen-parent rows. Pollination occurs from insects, mostly bees, carrying pollen from the pollen-parent to the female seed-parent plants, causing cross-pollination which results in $F_1$ hybrid-seeds. In addition, self-pollination and sib-pollination of the pollen-parent takes place. The mature production field is ultimately composed of rows with $F_1$ hybrid fruits on the seed-parent plants and rows with pollen-parent fruits. Only the $F_1$ hybrid fruits have commercial value as $F_1$ hybrid-seeds. The fruits of the pollen-parent have no commercial value and must be cleared from the hybrid seed production field before the harvest of the fruits of the seed-parent.

This current hybrid seed production method has two distinct disadvantages. First, one-third to one-fifth of the production field is used for planting of pollen-parent plants which bear useless fruits, thus reducing the efficiency of utilization of the field area. Second, the yield of the $F_1$ hybrid seed production is reduced because of inefficient insect pollination, which requires pollen transfer between plant rows, rather than within plant rows. Thus, it would be desirable to have an efficient $F_1$ hybrid cucumber seed production method which would overcome these drawbacks.

SUMMARY OF THE INVENTION

The invention relates to the production of $F_1$ hybrid-seeds in cucumber (*Cucumis sativus*). The present invention relates to a method wherein the pollen-parent bears only male-flowers and thus lacks the capability to bear fruit. The method comprises planting the hybrid-seed production field with a mixture of seed-parent and pollen-parent seeds and harvesting the desired $F_1$ hybrid cucumber seeds from the thus produced fruit on the seed-parent. The pollen-parent's inability to produce fruits has a two-fold advantage:

(1) Bee-pollination becomes more efficient because the two parental lines are not planted in separate rows; and
(2) The field produces only the commercially valuable $F_1$ hybrid seeds, rendering production more efficient and enabling a simple total harvest of the fruits.

The invention also relates to hybrid seed produced by the methods of this invention, the hybrid cucumber plant produced from the hybrid cucumber seed, and variants, modifications, and mutants thereof.

DETAILED DESCRIPTION OF THE INVENTION

The method of this invention comprises using cucumber lines which bear only male flowers as pollen-parents for the production of $F_1$ hybrid seeds. The male pollen-parent plants are unable to produce fruits. This trait of bearing only male flowers is termed androecious and is controlled by a recessive gene. R. Frankel and E. Galun, "Pollination Mechanisms," *Reproduction and Plant Breeding* (Springer-Verlag 1977), p. 281.

The androecious trait is introduced into any desirable breeding line to serve as the pollen-parent of a $F_1$ hybrid cucumber cultivar. In this invention, the male pollen-parent plant is contacted at the 4-leaf stage, before flowering, with an ethylene-releasing compound to induce the transient appearance of female flowers on the plant. This plant is then sib-pollinated. The fruit born by the plant has seed which produces male-only flower pollen-plants. These male-only flower pollen seeds are used as the pollen-parent line in $F_1$ hybrid seed production.

Ethylene-releasing compounds that may be used to induce the transient appearance of female flowers include ethaphon. The ethylene-releasing compounds are applied at a concentration effective to induce the transient appearance of the female flowers. These concentrations may be ascertained through routine screening methods, without undue experimentation. For example, ethaphon is typically applied to the plant at the concentration of 200 to 500 ppm.

In commercial production, the male pollen-parent plant is propagated in isolated pollen-parent production fields. Pollination of the transient female flowers by the pollen from male plants is achieved by insect pollination, typically by bringing beehives into the field to cause sib-pollination.

The fruits borne on the pollen-parent plant contain seeds that produce the androecious pollen-parent plant. The pollen-parent seeds are harvested for use in the production of the $F_1$ hybrid seed.

The seed-parent plant is propagated according to conventional cucumber hybrid-seed production methods. Frankel and Galan (1977), suora. Seeds of the seed-parent are planted in an isolated seed-parent production field. Before flowering occurs, about one-fourth to one-third of the plants are sprayed with a male-flower inducing agent which causes the transient production of male-flowers on the female plants. The male-flower inducing agent can conveniently be applied by spraying about one out of three or four rows of plants with the agent. Male-flower inducing agents are known and include gibberellic acid, silver salts such as silver nitrate, and anti-ethylenes such as AVG. The male-flower inducing agent is applied at a concentration effective to induce the transient appearance of male flowers. These concentrations may be ascertained through routine screening methods, without undue experimentation. For example, gibberellic acid is typically applied to the plant at a concentration of about 500 ppm. The female flowers are sib-pollinated with the pollen from the male flowers. Typically bees are employed to sib-pollinate the seed-parent production field. Fruits bearing seed-parent seeds are thus produced and the seed-parent seeds are harvested for use in the production of $F_1$ hybrid seed.

Thus, according to the methods of this invention, $F_1$ hybrid cucumber seed is produced from the pollination of the female flowers of the seed-parent plant from the pollen from the male flower pollen-parent plant to produce fruit bearing $F_1$ hybrid seed, and then harvesting the $F_1$ hybrid seed.

The $F_1$ hybrid seed production field is established in the following manner: Seeds of the seed-parent and of the pollen-parent are mixed at a desired ratio, typically between 10:1 and 5:1 of seed-parent:pollen-parent. These seeds are planted in isolated $F_1$ hybrid seed production fields. The female flowers of the seed-parent are pollinated with the pollen of the pollen-parent plant. At the beginning of flowering, it is advantageous to bring beehives into the field and retain them there for 3 to 6 weeks. After pollination, the seed-parent plants bear fruit with $F_1$ hybrid seeds, which are then harvested for recovering the $F_1$ hybrid seeds.

Further, this invention is directed to $F_1$ hybrid cucumber seeds produced according to the method of this invention, the hybrid cucumber plant produced from the hybrid cucumber seed, and variants, modifications, and mutants thereof. The terms variant, modification, and mutant refer to a hybrid seed or plant produced by the $F_1$ hybrid cucumber seed that is phenotypically similar.

The following examples further describe the materials and methods used in carrying out the invention. The examples are not intended to limit the invention in any manner.

EXAMPLE 1

To assess the applicability of the invention, an experimental hybrid seed production field was established. Soil preparation, seed planting, irrigation, mineral-fertilizer application, crop-protection management, and other horticultural operations were performed as customary in this art. Seed planting was in April which is the usual season for cucumber hybrid seed production in the Rehovot, Israel area, where the experiment was performed. A total area of 6000 m² was divided in experimental plots and the following three procedures of hybrid seed production were tested and the results evaluated.

(1) Conventional Methods of $F_1$ Cucumber Hybrid Seed Production.

(a) The monoecious pollen-parent was line Sh.
(b) The female seed-parent was line EN.
(c) There was a 1:4 ratio of pollen-parent:seed-parent plant rows, with one row of the monoecious pollen-parent between four rows of the female seed-parent.

(2) Androecious Pollen-Parent Plants and Female Seed-Parent Plants to Produce $F_1$ Cucumber Hybrid Seeds; 1:4 Pollen-Parent:Seed-Parent (a) The androecious pollen-parent (having only male-flowers) was line Er, which was isogenic to line Sh.
(b) The female seed-parent was line EN.
(c) Before planting, seeds of the pollen-parent were mixed with seeds of the seed-parent to provide a 1:4 (Er:EN) mixture.

(3) Androecious Pollen-parent Plants and Female Seed-Parent Plants to Produce $F_1$ Cucumber Hybrid Seeds; 1:3 Pollen-Parent:Seed-Parent (a) The androecious pollen-parent was line Er.
(b) The female seed-parent was line EN.
(c) Before planting, the seeds of the pollen-parent were mixed with seeds of the seed-parent to provide a 1:3 (Er:EN) mixture.

In all three tests, the seeds were planted in rows, of 60 m (length), spaced 0.90 m from each other.

Before flowering, the number of plants per unit length in the rows was equalized by retaining 4 plants per 1 m. After flowering beehives were placed adjacent to the field. The fruits were harvested from the rows of the seed-parent in procedure (1) and from all the rows in procedures (2) and (3). The hybrid seeds were extracted from the respective fruits, dried and weighed. The mean hybrid seed yields, per experimental plot were:

(1) 12.0 kg
(2) 16.0 kg
(3) 16.5 kg

Hence, there was a significantly higher seed yield by the method of the invention than by the conventional method of cucumber hybrid seed production. Mixing the pollen-parent and the seed-parent seeds in either the 1:4 or the 1:3 ratio did not provide significantly different yields of hybrid seeds.

EXAMPLE 2

To retest the applicability of the invention, the experiment described in Example 1 was repeated in the next year with the following changes:

(a) the androecious (male) line Er was used as pollen-parent in the conventional method (i.e., planted in separate rows) as well as in the procedure according to the invention;
(b) the plot size was doubled;
(c) the ratio of pollen-parent to seed-parent seed mixture was 1:10 (Er:EN).

The mean hybrid seed yields per plot were:

(1) by the convention procedure consisting of 1 row of pollen-parent to 4 rows of seed-parent: 25.25 kg.
(2) by the procedure of the invention consisting of planting a 1:10 (Er:EN) seed mixture in all the rows: 29.65 kg.

Thus, a clearly significant advantage in hybrid seed yield was obtained by the procedure of the invention.

Although the foregoing invention has been described in some detail by way of illustration and example for purposes of clarity of understanding, it will be obvious that certain changes and modifications may be practiced within the scope of the invention, as limited only by the scope of the appended claims.

What is claimed is:

1. A method for the production of $F_1$ hybrid cucumber seeds which comprises:

(a) growing a pollen-parent cucumber plant comprising an androecious plant which bears only male flowers and which does not produce fruit;
(b) growing a seed-parent cucumber plant which comprises a gynoecious plant which bears only female flowers and produces fruit;
(c) pollinating said seed-parent plant with pollen from said pollen-parent plant to produce fruit having $F_1$ hybrid seed; and
(d) harvesting said fruit and recovering the $F_1$ hybrid seed therefrom.

2. The method of claim 1 wherein said pollen-parent plant is propagated by (a) contacting an androecious cucumber plant at the 4-leaf stage before flowering with an ethylene-releasing compound to induce the transient appearance of female flowers and (b) sib-pollinating the plants to produce pollen-parent plant seeds.

3. The method of claim 2 wherein said ethylene-releasing agent is ethaphon.

4. The method of claim 1 wherein prior to growing, the seeds of the seed-parent and pollen-parent are mixed at a ratio of from 5:1 to 10:1 seed-parent:pollen-parent.

5. $F_1$ hybrid cucumber seed produced by the method of claim 1.

6. $F_1$ hybrid cucumber plant grown from the $F_1$ hybrid cucumber seed of claim 5.

* * * * *